United States Patent [19]

Timpl et al.

[11] Patent Number: 4,504,587

[45] Date of Patent: Mar. 12, 1985

[54] PROCEDURE FOR IMMUNOLOGIC DETERMINATION OF PROCOLLAGEN PEPTIDE (TYPE III) AND PROCOLLAGEN PEPTIDE COL 1 (TYPE III) TOGETHER AND A PROCESS FOR PREPARING ANTI-PROCOLLAGEN PEPTIDE COL 1 (TYPE III) SERUM

[75] Inventors: Rupert Timpl, Gauting; Dietrich Brocks, Hünfelden; Horst Neubauer, Königstein; Helmut Strecker, Pfungstadt, all of Fed. Rep. of Germany

[73] Assignee: Hoechst Aktiengesellschaft, Fed. Rep. of Germany

[21] Appl. No.: 474,457

[22] Filed: Mar. 11, 1983

[30] Foreign Application Priority Data

Mar. 13, 1982 [DE] Fed. Rep. of Germany ....... 3209149

[51] Int. Cl.$^3$ .................... G01N 33/52; G01N 33/54; G01N 33/56; A61K 39/00
[52] U.S. Cl. ........................................ 436/538; 435/4; 436/539; 436/540; 436/541; 436/542; 436/547; 436/800; 436/804; 436/811; 436/819; 436/824; 424/85
[58] Field of Search ............................... 436/538–542, 436/547, 800, 804, 819, 824; 424/85; 435/4, 7

[56] References Cited

U.S. PATENT DOCUMENTS 4,312,853  1/1982  Timpl ................... 424/1.1

FOREIGN PATENT DOCUMENTS 89008  9/1983  European Pat. Off. ............ 424/1.1

OTHER PUBLICATIONS

Bruckner et al, Chem. Abstracts, vol. 90 (1979) #17888b.

Hörkein et al., Proc. Natl. Acad. Sci. USA, vol. 78 (1981), pp. 6163–6167.

*Primary Examiner*—Christine M. Nucker
*Attorney, Agent, or Firm*—Finnegan, Henderson, Farabow, Garrett & Dunner

[57] ABSTRACT

The antigens procollagen peptide (type III) and procollagen peptide col 1 (type III) can be determined together immunologically by either (a) reacting a specified amount in each case of labeled procollagen peptide (type III) or procollagen peptide col 1 (type III) and a highly specific antiserum containing antibodies having affinity for both the antigens mentioned together with a sample having an unknown content of procollagen peptide (type III) and/or procollagen peptide col 1 (type III), separating off the antigen-antibody complex formed and measuring the amount of labeling in the complex and/or in the supernatant, or (b) bringing a specified amount of the highly specific antiserum to reaction with a sample having an unknown content of procollagen peptide (type III) and/or procollagen peptide col 1 (type III), fixing the unreacted amount of the antibody to procollagen peptide (type III) or procollagen peptide col 1 (type III) bound to a support, and bringing to reaction with a labeled second antibody, and then determining the amount of bound or excess second antibody by measuring the labeling. An anti-procollagen peptide col 1 (type III) serum is preferred as the highly specific serum, and this is obtained by using procollagen peptide col 1 (type III) for immunizing experimental animals and obtaining their serum.

16 Claims, No Drawings

PROCEDURE FOR IMMUNOLOGIC DETERMINATION OF PROCOLLAGEN PEPTIDE (TYPE III) AND PROCOLLAGEN PEPTIDE COL 1 (TYPE III) TOGETHER AND A PROCESS FOR PREPARING ANTI-PROCOLLAGEN PEPTIDE COL 1 (TYPE III) SERUM

The invention relates to a procedure for the immunologic determination of procollagen peptide (type III) and procollagen peptide col 1 (type III) together and a process for preparing anti-procollagen peptide col 1 (type III) serum.

Procollagen (type III) is a biosynthetic precursor form of a specific collagen (type III) which principally occurs in reticular connective tissue. It differs from this collagen (type III) by an additional peptide segment (procollagen peptide (type III) located at the amino end, which can be split off the molecule by treatment with collagenase. Procollagen peptide (type III) in turn can be further cleaved with collagenase to give the fragments col 1, col 2 and col 3 which can be isolated using known methods of protein chemistry (Nowack, H. et al., Eur. J. Biochem. 70, 205–216 (1976), Bruckner, P. et al., Eur. J. Biochem. 90, 595–603 (1978)).

Investigations into the concentration of procollagen peptide (type III) in the serum have shown that this concentration is raised in fibrotic disorders of the liver (Rhode, H. et al., Eur. J. Clin. Invest. 9, 451–459 (1979)). A radioimmunologic procedure to determine this antigen is described in European Pat. No. 4,940 (U.S. Pat. No. 4,312,853). It is also known that an antibody is obtained by immunizing rabbits with procollagen (type III) or procollagen peptide (type III), which antibody has a high affinity for procollagen peptide (type III). However, the affinity found for procollagen peptide col 1 (type III) was low (Rhode et al., Loc. cit.).

It has now been found, surprisingly, that antibodies are obtained by immunization with procollagen peptide col 1 (type III), which antibodies have the same affinity for procollagen peptide col 1 (type III) and for procollagen peptide (type III). Antibodies of this type can also be obtained by immunization with procollagen peptide (type III).

It was possible, using the method described in U.S. Pat. No. 4,312,853, to assay procollagen peptide (type III) in serum. The particular properties of the new antibodies now permit the total amount of the two antigens, procollagen peptide (type III) and procollagen peptide col 1 (type III), in body fluids to be determined using an immunologic procedure. Since the degradation product, col 1, is also bound by these antibodies, measurement of the sum of procollagen peptide (type III) and procollagen peptide col 1 (type III) permits an additional diagnostic conclusion. This signifies a valuable advancement in the art, particularly for disorders which are associated with increased proteolytic enzyme activities in the serum or in tissue. This is because the degradation product col 1 will be found in high amounts in the serum in such cases, but it has not been possible to assay col 1 with previous methods.

Thus, the invention relates to a procedure for immunologic determination of the two antigens—procollagen peptide (type III) and procollagen peptide col 1 (type III)—together, which comprises either (a) reacting a sample containing these antigens with a specified amount of a highly specific serum containing antibodies that have affinity for both antigens mentioned, which serum is in excess relative to the sample to be investigated, and with a specified amount of one of the two antigens in a labeled form; separating the antigen-antibody complex formed; and determining the amount of labeling in the complex and/or supernatant; or (b) reacting a sample containing these antigens with a specified amount of the highly specific serum, which serum is in excess relative to the sample to be investigated; fixing the unreacted amount of the antibody with a defined excess of one of the two antigens which is bonded to a support; reacting with a defined excess of a second labeled antibody; and determining the amount of labeling in the bound and/or free second antibody.

In this procedure, the various forms of radioimmunoassay (RIA) and enzyme-immunoassay can be used, and analogous types of labeling techniques such as fluorescence labeling and dye labeling also can be used. Radioactive labeling is preferred in variant (a) of the procedure and enzyme labeling is preferred in variant (b). Methods of this type are known to the expert and will not be dealt with in detail here. In these determination reactions, the labeled procollagen peptides compete for the antibodies in the manner described in U.S. Pat. No. 4,312,853 so that the amount of labeled antigen in the antigen-antibody complex formed decreases as the amount of unlabeled antigens in the sample increases. For this reason, either the labeling of the complex, for example by radioactivity or enzyme activity, or the labeling of the supernatant after separation of the antigen-antibody complex, can be used to establish the amount of antigen contained in the sample to be investigated. This is done by means of a calibration curve drawn up with samples of known content of procollagen peptide (type III) or procolagen peptide col 1 (type III). The labeling in the complex is preferably determined in variant (b) of the procedure, but can also be done in variant (a).

Separation of the antigen-antibody complex from the solution can be carried out by the customary methods known to the expert for this purpose, such as filtration, filtration with suction, centrifugation and the like. It is also possible to employ the antiserum bound to a solid support, for example the inner wall of a test tube.

The procedure is preferably carried out such that the separation of the antigen-antibody complex formed with the highly specific anti-procollagen peptide col 1 (type III) serum from the unreacted antigen is done by using a second antibody directed against the highly specific serum. In this instance, an antibody against γ-immunoglobulin of the animal species used for obtaining the antiserum is preferred. The labeling of the antigen, i.e. procollagen peptide (type III) or procollagen peptide col 1 (type III) can be carried out by the methods known for labeling proteins. For radioactive labeling, the use of the radionuclide iodine-125 is preferred. The chloramine T method (McConahey, P.J. et al., Int. Arch. Allergy 29 (1966) 185) is preferred for labeling with this radionuclide.

The enzyme-immunoassay variant for determining procollagen peptide (type III) and procollagen peptide col 1 (type III) can also be carried out in such a manner that the antibody against γ-immunoglobulin of the relevant animal species, for example from rabbits, is enzyme-labeled. In this type of enzyme-immunoassay, the part of the anti-procollagen peptide serum remaining after formation of the antigen-antibody complex is determined by binding it to procollagen peptide (type III)

or procollagen peptide col 1 (type III) bound to a support and then reacting it with enzyme-labeled antibody against the rabbit γ-immunoglobulin.

The amount of bound enzyme-labeled antibody is then determined by measurement of the enzyme reaction, and it is directly proportional to the unknown amount of procollagen peptide (type III) and procollagen peptide col 1 (type III) in the sample.

It is crucial for the method of determination according to the invention that a suitable antiserum against procollagen peptide col 1 (type III) be available. This antiserum also has affinity for procollagen peptide (type III).

Procollagen peptide col 1 (type III) is advantageously used for immunization. The immunization can be carried out by subcutaneous injection of procollagen peptide col 1 (type III) into experimental animals, such as goats or preferably rabbits, in the presence of complete Freund's adjuvant. The dose of antigen per animal in this case is 0.2–0.5 mg.

The following examples illustrate the invention further.

EXAMPLE 1

Preparation of procollagen peptide col 1 (type III)

60 mg of procollagen peptide (type III) are dissolved in the required amount of a buffer (buffer 1: 0.05 M tris.HCL, ph 8.0, 0.02 M $CaCl_2$) and heated to 55° C. After addition of 420 units of collagenase the mixture is incubated at 55° C. for 15 min. After cooling down to 37° C. and addition of 420 units of collagenase, the incubation is continued for 3 hours. The mixture is then dialyzed against two buffers (buffer 2: 0.005 M tris.HCL, ph 8.6, 2 M urea; buffer 3: 0.005 M tris.HCL, ph 8.6, 8 M urea) and applied to a DEAE cellulose column (1.6×5 cm) equilibrated with buffer 3. The proteins bound to the column are eluted with an NaCL gradient (0–0.3 M). The eluate is monitored in respect of the absorption at 230 nm and the antigen activity by using antibodies which are specific for procollagen peptide (type III). The last peak eluted from the column normally contains procollagen peptide col 1 (type III). The peptide is desalted by dialysis against 0.01 M $(NH_4)_2CO_3$ and is freeze dried.

Performance of the immunologic determination (RIA)

25 μg of procollagen peptide (type III) are labeled with 1 millicurie of iodine-125 by the chloramine T method and non-bound iodine is removed by dialysis. The subsequent steps in performing the radioimmunoassay are preferably carried out in the presence of 0.04% of a nonionic detergent, such as ®Tween 20. Binding curves are determined using 2 ng in each case of labeled procollagen peptide (type III) or procollagen peptide col 1 (type III). The concentration of the total amount of procollagen peptide (type III) and procollagen peptide col 1 (type III) in an unknown sample of serum or other body fluids is determined by using the following inhibition test.

A specified amount of the antibody is preincubated with the unknown sample at 4° C. for 16 hours and, after addition of 2 ng of labeled peptide, is incubated at 4° C. for a further 8 hours. Then an excess of antibodies against rabbit immunoglobulin is added and the antigen bound in the immunocomplex is separated out of the solution. The inhibitory activity of the unknown sample is compared with the activity of standard concentrations of unlabeled procollagen peptide (type III) or procolagen peptide col 1 (type III).

When the sample employed in the inhibition test is serum from a healthy patient, the values found for procollagen peptide col 1 (type III) plus procollagen peptide (type III) are typically about 3 times those which have been found using a RIA for procollagen peptide (type III).

EXAMPLE 2

Immunologic determination using enzyme-immunoassay

The concentration of procollagen peptide (type III) and procollagen peptide col 1 (type III) in an unknown sample of serum or other body fluids is determined using the following enzyme-immunoassay.

A specified amount of the anti-procollagen peptide col 1 (type III) serum is preincubated with the unknown sample at 4° C. for 2.5 hours. The mixture is then pipetted into a well of a microtiter plate coated with 20 ng of procollagen peptide (type III) and incubated at 4° C. for 18 hours. After pouring off the supernatant and washing the wells with physiological saline, a specified amount of enzyme-labeled antibody (for example, peroxidase-labeled) against γ-immunoglobulin of the rabbit is added and incubation is carried out at room temperature for 5 hours. After pouring off the supernatant and washing with physiological saline, the enzyme reaction is started by the addition of enzyme substrate ($H_2O_2$ in the case of peroxidase-labeling) and chromogen (for example o-phenylenediamine). After 30 min. incubation at room temperature, the reaction is stopped by addition of 50 μliter of 6 M HCL. The color intensity of the solution is determined after 30 min. using a suitable photometer. This color intensity is directly proportional to the amount of bound enzyme-labeled antibody and thus to the unknown amount of procollagen peptide (type III and procollagen peptide col 1 (type III) in the sample. Using a calibration curve, which has been drawn up using solutions of known content of procollagen peptide (type III) or procollagen peptide col 1 (type III), the amount of procollagen peptide (type III) plus procollagen peptide col 1 (type III) in the sample can then be found.

We claim:

1. A method for the simultaneous immunologic determination of the two antigens, procollagen peptide (type III) and procollagen peptide col 1 type III), which comprises:
   a. reacting a sample containing said two antigens with a specified amount of a serum containing antibodies that have affinity for both of said antigens, which specified amount of said serum contains an excess of said antibodies relative to the amount of said antigens in said sample, whereby an antigen-antibody complex is formed; and
   b. quantifying the amount of said antibodies forming said antigen-antibody complex with said two antigens in said sample.

2. A method as recited in claim 1, wherein said step of quantifying the amount of said antibodies forming an antigen-antibody complex with said two antigens in said sample comprises:
   a. reacting, in addition to said sample containing said two antigens, a specified amount of one of said antigens in a labeled form with said serum; and b. separating the resulting product into an antigen-antibody complex and a supernatant.

3. The method as recited in claim 2, wherein quantifying the amount of said antibodies forming an antigen-antibody complex with said two antigens in said sample comprises the further step of determining the amount of labeled antigen present in said complex.

4. A method as recited in claim 2, wherein quantifying the amount of said antibodies forming an antigen-antibody complex with said two antigens in said sample comprises the further step of determining the amount of labeled antigen in said supernatant after separation of said complex and said supernatant.

5. A method as recited in claim 1, wherein said step of quantifying the amount of antibodies forming an antigen-antibody complex with said antigens in said sample comprises:
   a. fixing the unreacted amount of said antibodies with a defined excess of one of said two antigens bonded to a support;
   b. reacting the unreacted amount of said one of said two antigens bonded to a support with a defined excess of a labeled second antibody to form free labeled second antibody and a complex of said labeled second antibody with said one of said two antigens bonded to a support.

6. A method as recited in claim 5, wherein quantifying the amount of said antibodies forming said antigen-antibody complex with said two antigens in said sample comprises the further step of determining the amount of said labeled second antibody present in said complex of said labeled second antibody with said one of said two antigens bonded to a support.

7. A method as recited in claim 5, wherein quantifying the amount of said antibodies forming said antigen-antibody complex with said two antigens in said sample comprises the further step of determining the amount of free labeled second antibody present.

8. A method as recited in claim 1, 2, 3, 4, 5, 6, or 7, wherein said serum is an anti-procollagen peptide col 1 (type III) serum.

9. A method as recited in claim 2, 3, or 4 wherein said labeled antigen is radioactive, enzyme, or fluorescence labeled.

10. A method as recited in claim 5, 6, 7, wherein said labeled second antibody is radioactive, enzyme, or fluorescence labeled.

11. A method as recited in claim 2, 3, or 4, wherein said separation of said antigen-antibody complex is accomplished with a second antibody having an affinity for said antibodies.

12. A method as recited in claim 2, 3, or 4, wherein said labeled antigen is radioactive labeled.

13. A method as recited in claim 12, wherein said labeling is accomplished with iodine-125.

14. A method as recited in claim 5, 6, or 7, wherein said labeled second antibody is enzyme labeled.

15. A process for preparing a highly specific anti-procollagen peptide col 1 (type III) serum, which comprises immunizing experimental animals with procollagen peptide col 1 (type III) and obtaining their serum.

16. Anti-procollagen peptide col 1 (type III) serum obtained by the process claimed in claim 15.

* * * * *